(12) United States Patent
Tobinick (10) Patent No.: US 6,168,589 B1
(45) Date of Patent: *Jan. 2, 2001

(54) APPARATUS AND METHOD EMPLOYING A SINGLE LASER FOR REMOVAL OF HAIR

(76) Inventor: Edward L. Tobinick, 100 UCLA Medical Plz., Suite 205, Los Angeles, CA (US) 90024-6903

(*) Notice: Under 35 U.S.C. 154(b), the term of this patent shall be extended for 0 days.

This patent is subject to a terminal disclaimer.

(21) Appl. No.: 09/054,574

(22) Filed: Apr. 3, 1998

(51) Int. Cl.[7] .................................................. A61B 18/18
(52) U.S. Cl. ........................... 606/9; 606/3; 606/10; 606/16; 606/19
(58) Field of Search ........................... 606/2, 3, 9, 10, 606/11, 12, 13, 16, 17, 18, 19

(56) References Cited

U.S. PATENT DOCUMENTS

| | | | |
|---|---|---|---|
| 4,791,927 | * | 12/1988 | Menger .................................... 606/10 |
| 5,150,704 | * | 9/1992 | Tatebayashi et al. .................... 606/10 |
| 5,658,323 | * | 8/1997 | Miller ....................................... 606/9 |
| 5,662,644 | * | 9/1997 | Swor ........................................ 606/9 |
| 5,717,806 | * | 2/1998 | Pileski et al. ........................... 606/16 |
| 5,843,072 | * | 12/1998 | Furumoto et al. ....................... 606/9 |
| 5,873,875 | * | 2/1999 | Altshuler ................................ 606/10 |
| 5,989,243 | * | 11/1999 | Goldenberg ............................. 606/1 |
| 6,001,091 | * | 12/1999 | Murphy-Chutorian et al. ......... 606/1 |

* cited by examiner

*Primary Examiner*—Linda C. M. Dvorak
*Assistant Examiner*—Bryan K. Yarnell
(74) *Attorney, Agent, or Firm*—Ezra Sutton (57) ABSTRACT

A laser apparatus and method for permanently removing a plurality of hair follicles from the skin of a patient. The laser apparatus includes a housing having a single laser for sequentially emitting a series of pulses of coherent light energy having a pulse width in the range of ½ ms to 40 ms; a fiber optic bundle connected to the laser for transmitting said series of pulses of coherent light energy to the skin of a patient; and a sequence control device for controlling the laser to emit the series of pulses of coherent light energy sequentially, with a time delay of less than 100 milliseconds between the sequential pulses of the single laser. The laser apparatus includes a handpiece assembly for holding a section of the fiber optic bundle for directing the series of pulses of coherent light energy to the same spot of the patient's skin to remove the plurality of hair follicles, veins, or capillaries.

25 Claims, 10 Drawing Sheets

APPARATUS AND METHOD EMPLOYING A SINGLE LASER FOR REMOVAL OF HAIR

FIELD OF THE INVENTION

This invention relates to an improved laser apparatus and method employing a single laser and a sequence control device for removal of hair, or veins or capillaries, and more particularly, it relates to a single laser emitting a series of sequential pulses of coherent light energy, which are transmitted to the same area of the skin through a common optical delivery system.

BACKGROUND OF THE INVENTION

Hair removal by lasers is a new clinical field developed in the early nineties and only commercially available to patients since 1996. Lasers allow the rapid removal of large areas of hair, veins or capillaries on almost any body area, such as on the face, arms, legs, breasts, hands, stomach and the like. Laser treatment provides an unusually low discomfort level to the patient, and hair removal may last for weeks on a body area. However, all of the current lasers used for hair removal are problematic and produce unwanted side effects such as burning the skin, changes in skin pigmentation, and sometimes permanent scarring.

The currently available lasers use different approaches to hair removal, and use different laser technologies. For example, the ND:YAG laser was the first commercially available laser, but is the least effective, and does not provide permanent hair removal. The ruby laser emits a fixed wavelength of 694 nm, but has a propensity to burn the skin of the individual being treated. Because of this problem, ruby lasers cannot be used to treat olive-skinned or tanned individuals. The alexandrite laser emits a fixed wavelength of 755 nm (near the infrared spectrum), but has a propensity to burn the skin of the individual being treated, and is less effective than ruby laser treatment. Also, lasers presently being used do not consistently and reliably provide permanent hair removal, they require multiple treatments, and often burn the skin.

Pulsed flashlamps emit filtered visible light having wavelengths in the range of 550 nm and above, but have not been effective in providing permanent hair removal.

Current cutaneous lasers work by delivering energy in the form of laser light which is absorbed by the cutaneous target, heating the target and thereby causing its destruction. Different skin structures have different colors, different surface to volume configurations, and other factors which cause differential rates of heat loss. All of the hair removal lasers work by application of the principal of selective photothermoloysis, i.e. selective destruction due to heat caused by absorption of light. Laser light, which has a single wavelength, is optimally absorbed by a target which has a complementary specific color. This laser target is called a chromophore. The usual chromophore for hair removal lasers is melanin, found in high concentration in brown and black hair, and is responsible for the color of hair.

The clinical problem is that melanin is also found in the epidermis, and is responsible for native skin color and tan. Laser energy is therefore also absorbed into the epidermis. The problem of hair removal by lasers therefore is to deliver laser energy that heats the hair to a sufficient degree to cause permanent damage and hair loss, yet spare the skin of any damage. Present lasers are unable to accomplish this. For example, ruby lasers work in removing hair follicles because the wavelength of 694 nm which is emitted, is selectively absorbed by melanin and less so by other cutaneous structures, such as blood vessels. In fair skin, with little melanin, selectivity is sufficient to allow sparing of the skin and destruction of hair with even a single pulse. Alexandrite lasers perform similarly, but since their absorption by melanin is somewhat lower they seem to be less effective than ruby lasers, at least in their current forms.

The Cynosure® laser adds another approach, which they call Thermokinetic Selectivity™. This means the selective destruction of the target with the same chromophore as the skin (i.e. melanin), due to less efficient heat conduction out of the hair (as compared with the epidermis). This less efficient heat conduction is due to a variety of factors, the main one being the unfavorably large volume to surface area of the hair. The Cynosures® laser, like the ruby lasers, uses a single pulse, but the pulse used by this alexandrite laser is longer (5–20 ms). This longer pulse allows more gradual accumulation of heat by the skin, so the heat has time to dissipate (cool) and to prevent burning of the skin. This technique improves safety, but the technique is not able to deliver enough heat to provide permanent hair loss, and some burns still occur.

The use of medical lasers to produce permanent hair removal in patients with hairs of all colors, and skin of all colors, has, up to this time, been impossible to achieve with current technology. While promising, the currently-used lasers have all been unable to treat patients with dark skin. In addition, even in Caucasian patients, the currently-used lasers have burned many patients, leading to prolonged changes in skin color and even, in some cases, to permanent scarring. Hair loss, although usually prolonged, has not been permanent for the majority of patients.

Nevertheless, the use of monochromatic (laser) light in the range of 694 to 900 nm still appears to be the most effective way to achieve long-term hair removal. To achieve predictable permanency we need to achieve higher temperatures in the hair without heating the epidermis to the point where it is burned. The single pulse techniques described above are inadequate to accomplish this.

There remains a need for an improved laser apparatus and method which will supply a series of laser energy pulses with relatively short time delays between pulses to heat a hair follicle sufficiently to cause permanent damage to that hair follicle, and yet spare the skin from burning, thus providing a safe and permanent method of hair removal.

A new laser has been developed that has the following major advantages: 1) increased efficacy, causing greater hair loss and true permanent hair removal; 2) increased safety, with burning of the skin eliminated, so that treatment has no side effects; 3) increased speed of treatment, nearly by a factor of two; and 4) it allows the use of laser hair removal for patients with dark skin, thereby greatly increasing the range of people who can be treated with this technology.

DESCRIPTION OF THE PRIOR ART

Laser apparatus and methods for hair removal having various structures have been disclosed in the prior art. For example, U.S. Pat. Nos. 5,630,811 and 5,658,323 to Miller disclose a method and apparatus for dermatology treatments for lesions and hair removal using a modified laser device. The specific target for the laser radiation is the melanin within the hair shaft and within the melanocytes lining of the follicular duct. Pulse width is controlled to provide a direct thermal effect from a single pulse.

U.S. Pat. No. 5,647,866 to Zaias discloses a method of hair depilation through the application of pulsed laser energy having a wavelength readily absorbed by hemoglobin. The process of selective photothermoloysis is used by the laser to focus on a particular region in the epidermis to be irradiated. The pulse duration or time period (30 to 40 nanoseconds) is shorter than the thermal relaxation time for melanin in hair.

U.S. Pat. No. 5,683,380 to Eckhouse discloses a method and apparatus for removing hair (depilation) using a single high intensity pulsed flashlamp (not a laser) which emits a broad spectrum of pulsed incoherent light that is polychromatic. Because of the broad spectrum of wavelengths emitted by the flashlamp, only part of the light energy is absorbed by the hair, making it inefficient for permanent hair removal, although it does provide temporary hair loss.

None of these prior art patents disclose the particular structure of the present invention of a laser apparatus and method using a single laser and a sequencer for safe and permanent hair removal.

Accordingly, it is an object of the present invention to provide an improved laser apparatus and method which supplies a series of high level laser energy pulses from a single laser to heat a hair follicle and hair follicle shaft to cause permanent damage to that hair follicle and shaft, and yet spare the skin from burning, thus providing a safe and permanent method of hair removal.

Another object of the present invention is to provide an improved laser apparatus employing a single laser, controlled by a sequence control device, and a fiber optic cable which sequentially emits a series of pulses of coherent light energy from the fiber optic cable for permanently removing a plurality of hair follicles, veins or capillaries from the skin area of a patient.

Another object of the present invention is to provide an improved laser apparatus having a handpiece for ease of use by the operator in directing the series of laser pulses at the skin to rapidly remove large areas of hair on almost any body area, such as on the face, hands, arms, legs, breasts, stomach and the like, where such treatment provides a low discomfort level to the patient.

Another object of the present invention is to provide an improved laser apparatus and method for treatment of other cutaneous conditions (in addition to hair), such as the treatment of leg veins, spider veins, angiomas, lesions, other vascular anomalies and other dermatological conditions effecting the skin of a patient.

Another object of the present invention is to provide a single pulsed laser and a sequence control device for emitting laser energy through an optical delivery system which delivers a series of sequential pulses from the single pulsed laser.

Another object of the present invention is to provide an improved laser apparatus and method for adjusting pulse width and the time delay between pulses to customize treatment and the energy delivered to the spot being treated according to skin color, hair color, hair diameter and the anatomic site being treated.

Another object of the present invention is to provide safe and permanent hair removal in a wider range of patients having hairs of all colors and skin of all colors, including patients with dark skin. Generally, the present invention will accommodate all persons having hair which is darker than their skin.

Another object of the present invention is to provide a delay between laser pulses which is shorter than the thermal relaxation time of the hair being treated, so the hair does not cool off between pulses, and wherein the delay between laser pulses is longer than the thermal relaxation time of the skin, so the skin may dissipate heat and cool off between pulses and does not burn.

Another object of the present invention is to provide a method and apparatus wherein the pulse width and delay between pulses may be varied to accommodate the thermal relaxation time of each patient's hair and skin.

Another object of the present invention is to provide an improved laser apparatus and method that is easy to use, and the laser apparatus is durable, light-weight and easily maintained.

Another object of the present invention is to provide an improved laser apparatus that provides a wider beam area (spot size on the skin) by utilizing a single pulsed laser and a sequence control device for delivering more laser energy to each spot allowing the spot size to be made larger for faster treatment.

A further object of the present invention is to provide an improved laser apparatus that is simple to manufacture and assemble in an economical manner, and is cost effective for the user.

SUMMARY OF THE INVENTION

In accordance with the present invention, there is provided a laser apparatus for permanently, safely, and quickly removing a plurality of hair follicles, veins, capillaries or blood vessels from the skin of a patient; including patients with dark skin. The laser apparatus includes a housing having a single laser for emitting a series of pulses of coherent light energy having a pulse width in the range of ½ ms to 40 ms; a multi-strand fiber optic bundle connected to the laser for transmitting a series of pulses of coherent light energy to the skin of a patient; and a sequence control device for controlling the laser to emit the series of pulses of coherent light energy sequentially, with a time delay between pulses being less than the thermal relaxation time of the hair being treated, which typically is less than 100 milliseconds between the sequential pulses of the single laser. The laser apparatus includes a handpiece assembly for holding a section of the fiber optic bundle for directing the series of pulses of coherent light energy to the same spot of the patient's skin to remove the plurality of hair follicles, veins, or capillaries, or blood vessels. In alternate embodiments, other optical delivery systems may be employed. These may include an articulated laser arm assembly, or a light path or pipe for a diode laser.

A method of removing hair or blood vessels from the skin of a patient using a laser apparatus having a single laser, a sequence control device and an optical delivery system, which includes the steps of controlling the single laser to sequentially emit a series of pulses of coherent light energy, transmitting the series of pulses of coherent light energy through the optical delivery system to the same spot on the skin of the patient, irradiating the same spot on the skin containing the hair or blood vessels with the sequential pulses of coherent light energy transmitted through the optical delivery system from the laser, and pulsing the laser at least two or more times through the optical delivery system at a wavelength in the range of 550 to 1200 nm, at a power level in the range of 5 to 80 Joules/cm$^2$, at a pulse duration in the range of ½ to 40 milliseconds, having a pulse delay in the range of 5 to 100 milliseconds, and having a beam diameter on the treatment area in the range of 4 to 50 millimeters.

The new technology requires that high energy laser pulses be delivered in rapid succession to exactly the same area of the skin. The maximal energy is delivered to the hair germinative apparatus using two or more long sequential pulses from the single laser, with the pulses repeated at a time interval shorter than the thermal relaxation time of the hair being treated. For most patients, this means two or more high-energy (10–40 Joules/cm$^2$) long duration (2 to 30 milliseconds) pulses, separated by 10 to 30 milliseconds, each with a large (e.g., 10 millimeters or greater) spot size. None of the currently-produced lasers are able to produce these results. The 10 to 30 milliseconds delay between pulses must be selected to be shorter than the thermal relaxation time of the hair being treated, so the hair does not cool off between the pulses.

For example, short pulse duration lasers (with a pulse duration measured in nanoseconds) can repeat rapidly, but these are not suitable for optimal hair removal. All of the new hair removal lasers (ruby, alexandrite, diode) are long pulse lasers. Most of these recycle every 1000 milliseconds, with the fastest recycling every 200 milliseconds. The repetition rate that is necessary, however, is over ten times faster. The new laser apparatus of the present invention is able to accomplish these goals.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED EMBODIMENT

Figure 1:
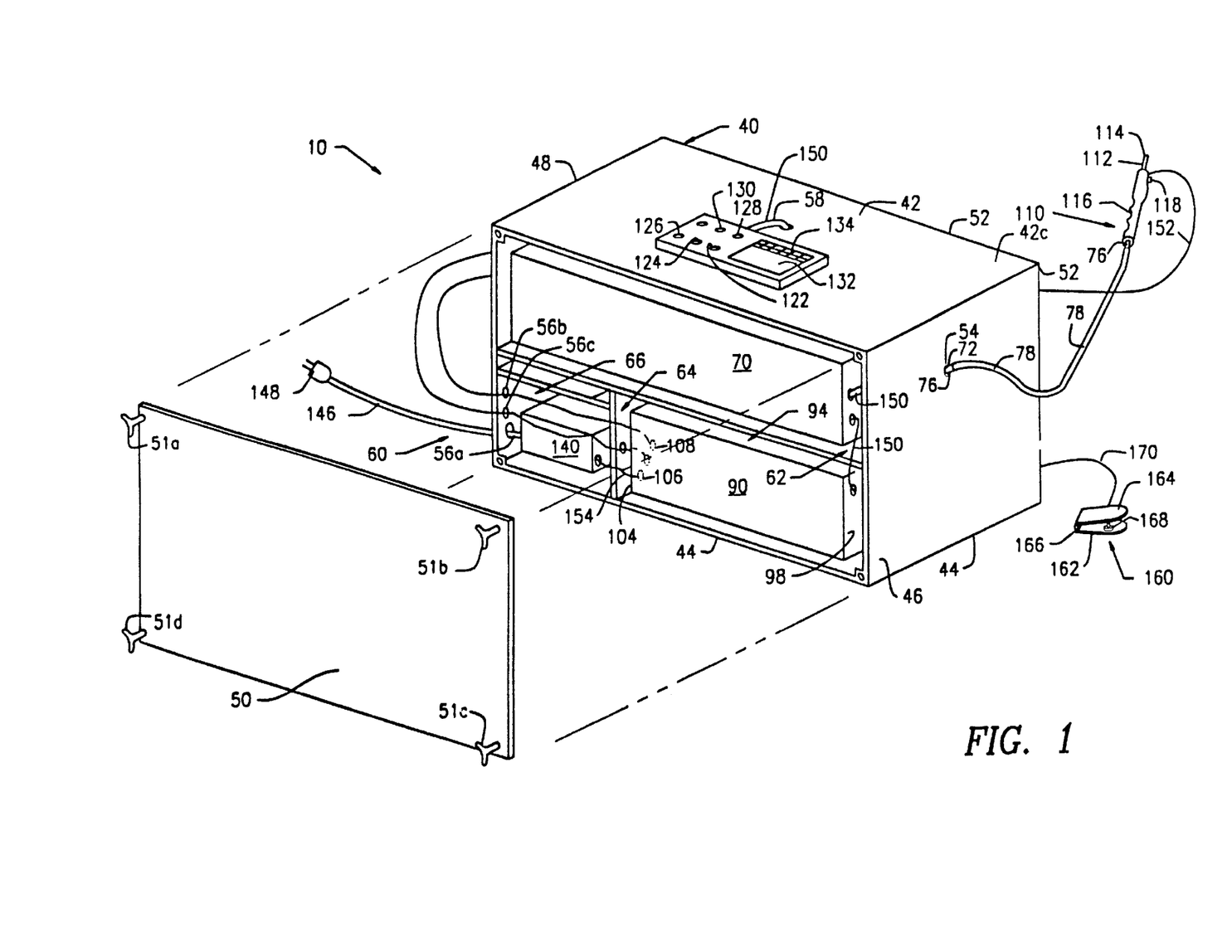
FIG. 1 is a perspective view of the laser apparatus of the preferred embodiment of the present invention showing the housing, having a control panel thereon, the single laser, the flexible conduit having a fiber optic bundle therein, the laser handpiece having thereon an operating pulse firing button, and the foot pedal switch assembly having an activation firing button thereon, shown in an operational mode.
Figure 1A:
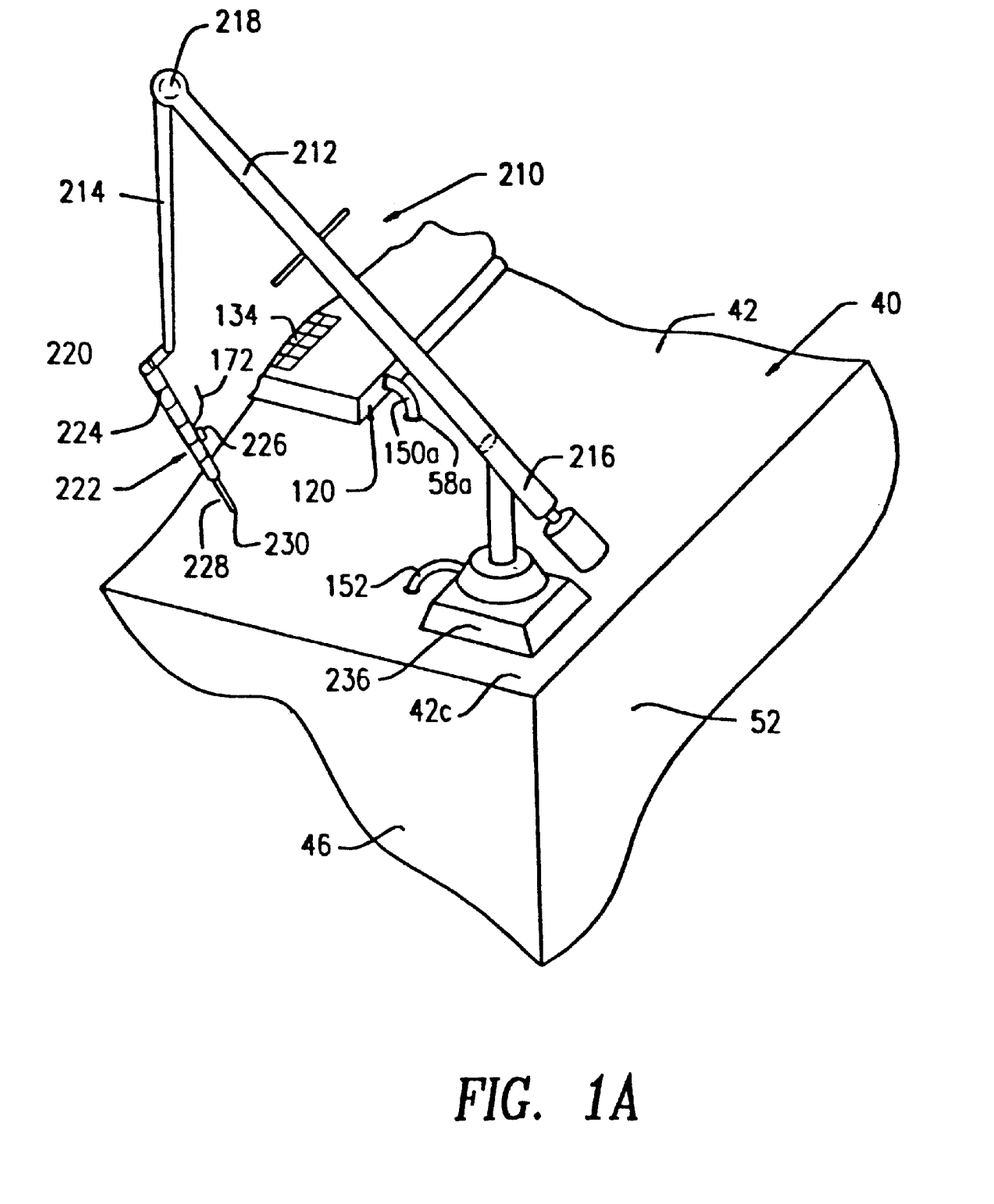
FIG. 1A is a perspective view of the laser apparatus of the present invention showing the articulated laser arm assembly and its component parts thereon.
Figure 2:
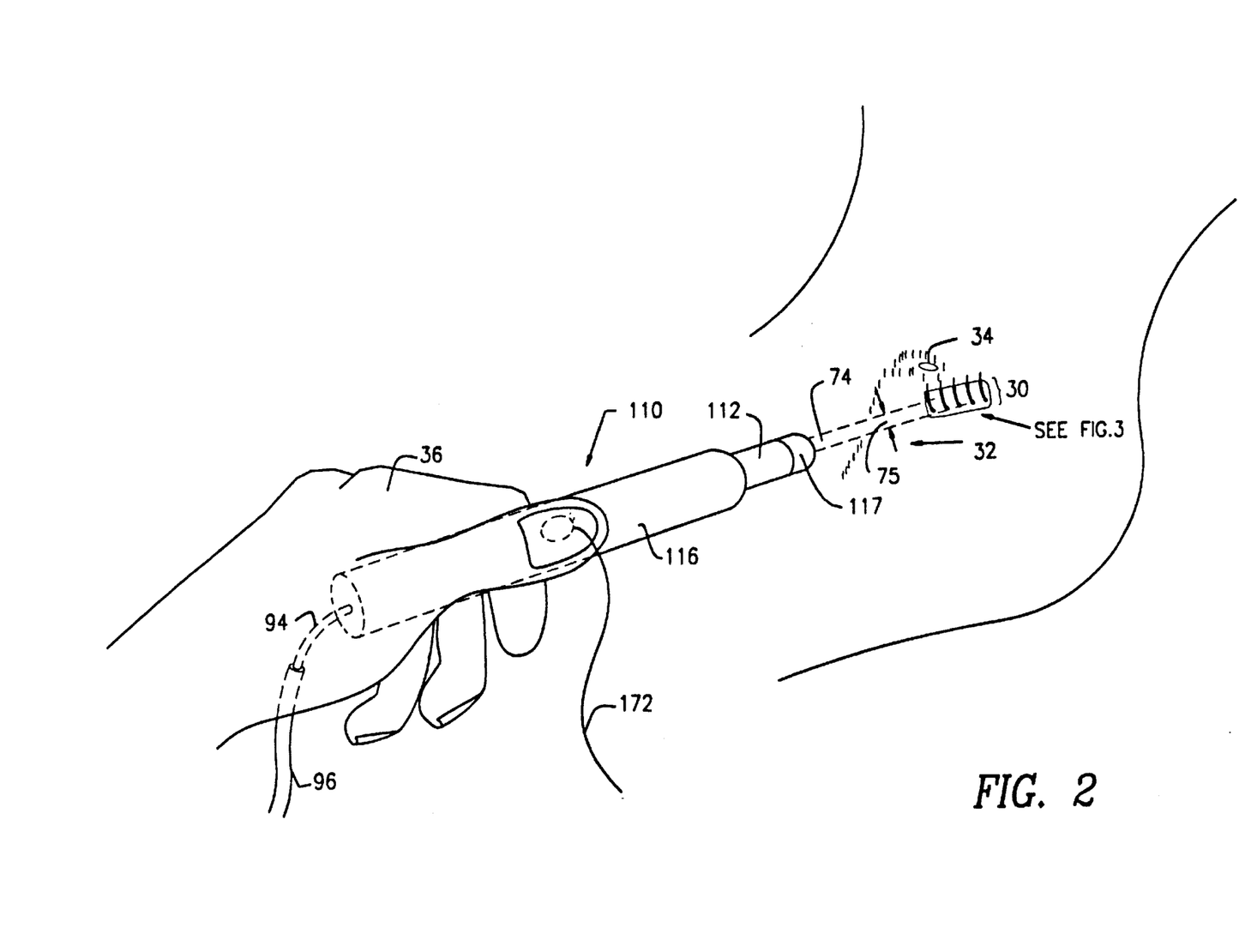
FIG. 2 is an enlarged perspective view of the laser apparatus of the present invention showing the flexible conduit and the laser handpiece having a pulse firing button thereon, shown in an operational mode.

The improved laser apparatus 10 and method thereof for permanently removing a plurality of hair follicles 20 from a patient's skin area 14, or for removing blood vessels 28 such as veins and capillaries, are represented in detail by FIGS. 1, 1A, 2 through 5A to 5H and 6. The laser apparatus 10 of the present invention, as shown in FIGS. 1 and 2 of the drawings, includes a laser housing 40 having therein a laser device 70, a sequence control device 90 and an electrical panel box 160. Additionally, laser apparatus 10 also includes an optical delivery system having fiber optic bundle 76 connected to the laser device 70. Fiber optic bundle 76 is connected to a laser handpiece 110 having a pulse firing button 118 thereon. Handpiece 110 is attached at one end 95a to the fiber optic bundle 76.

Laser housing 40, as shown in FIG. 1, includes a top wall 42, a bottom wall 44, a front wall 46, a rear wall 48, and side walls 50 and 52, all being integrally connected to form a substantially rectangular shaped configuration which forms an interior chamber 60. The interior chamber 60 includes a first compartment 62 for holding and containing therein the single laser device 70, a second compartment 64 for holding and containing therein the sequence control device 90 and a third compartment 66 for holding and containing therein the electrical panel box 140.

Figure 6:
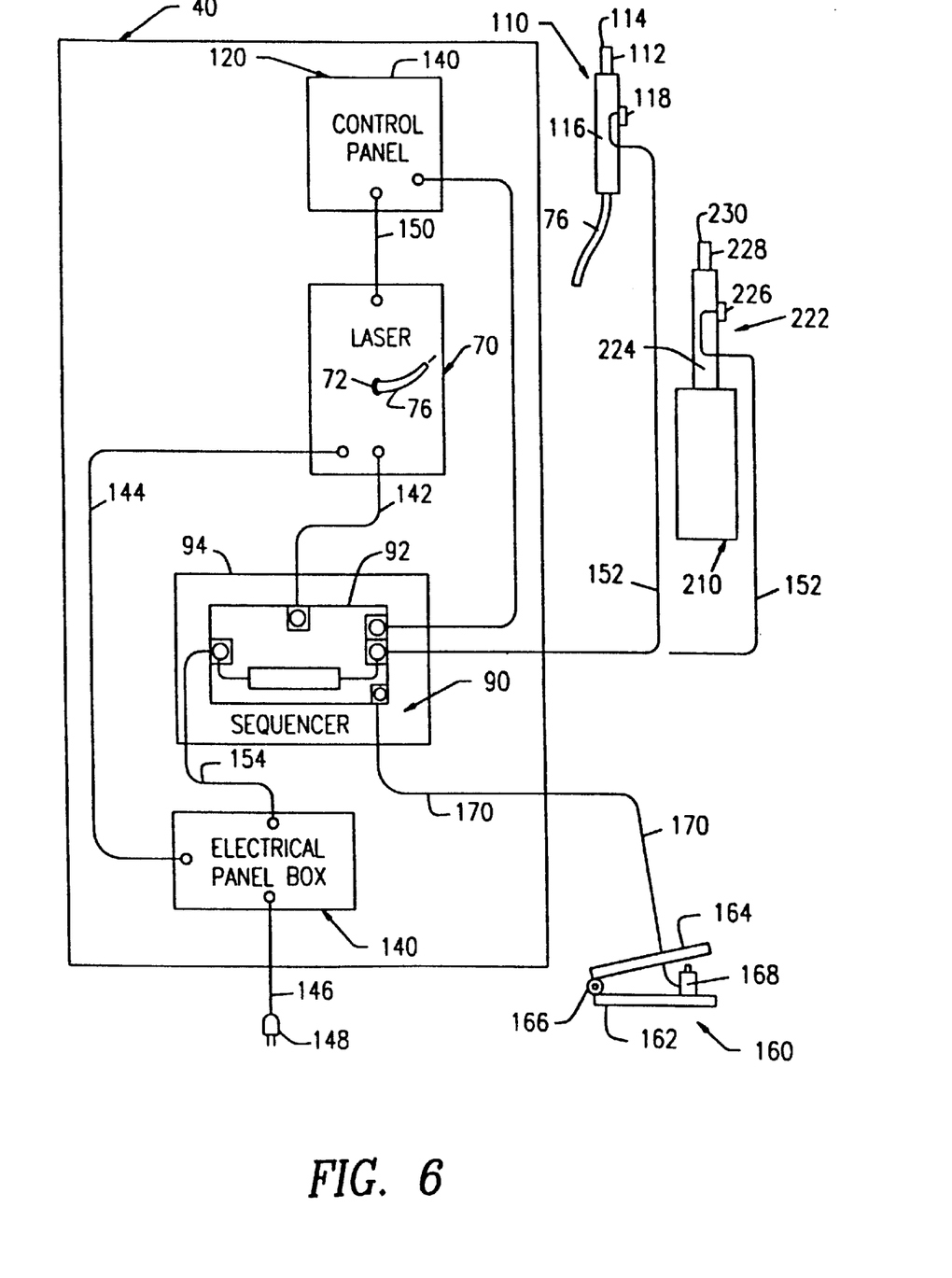
FIG. 6 is an electrical schematic block diagram of the laser apparatus of the present invention showing the electrical connections of the major component parts therein.

Single laser device 70, as shown in FIG. 1, includes a laser projector lens 72 of a specific wavelength for producing a coherent laser beam 74 having a laser beam diameter 75 of a given width. The laser projector lens 72 is attached to the fiber optic bundle 76 for transmitting pulses of coherent light energy (laser beam 74) from the single laser device 70 through the fiber optic bundle 76. Single laser device 70 is electrically connected to the laser sequence control device 90, to the laser programmable control panel 120, and to the electrical panel box 140 via electrical lines 142, 150, and 144, respectively, as shown in FIG. 6.

The single laser device 70 is adjustable for energy level (Joules/cm$^2$), pulse width duration (ms), delay time between pulses (ms), spot size (mm) and wavelength (nm) via the laser programmable control panel 120.

Laser device 70 may be selected from the group consisting of an alexandrite laser, a ruby laser, a diode laser, an infrared laser, an ND:YAG laser, and the like. An alexandrite laser has a specific wavelength of 755 nm; a ruby laser has a specific wavelength of 694 nm, a diode laser can be set at any wavelength in the range of 550 to 900 nm; an ND:YAG laser has a specific wavelength of 1064 nm. The most effective wavelengths for permanent hair removal are in the range of 550 nm to 900 nm when using the alexandrite, ruby or diode laser.

Figure 3:
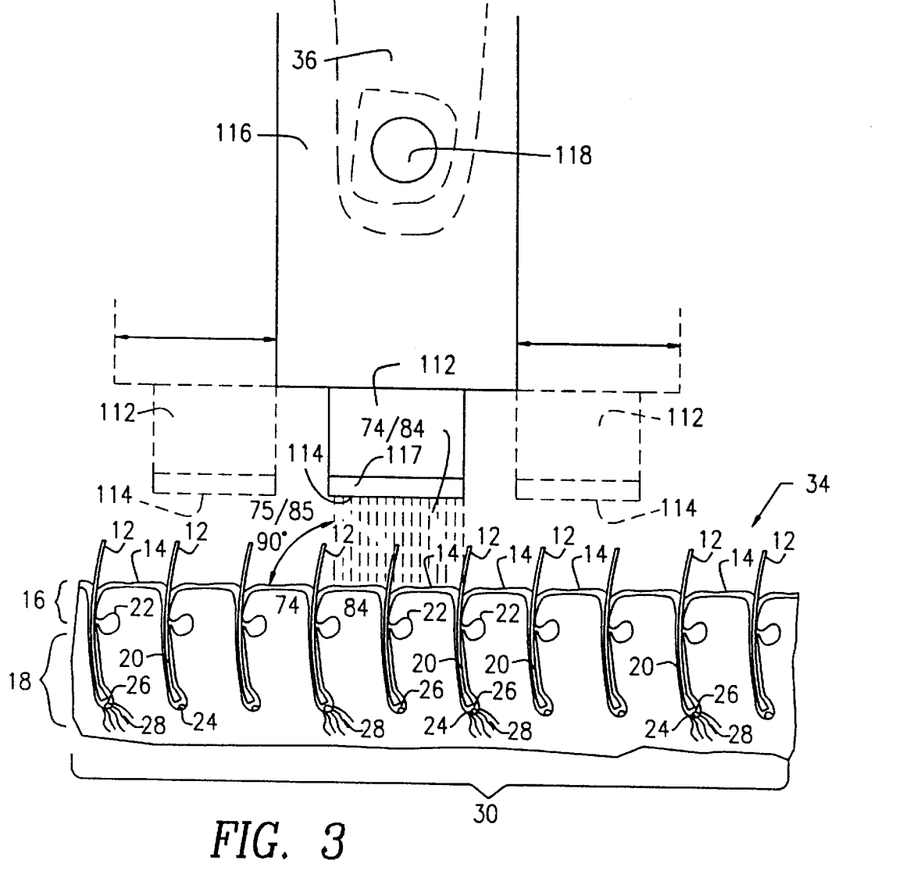
FIG. 3 is a cross-sectional view of a plurality of hair shafts within a region of skin tissue being irradiated with a laser beam from the laser handpiece of the present invention.

The laser sequence control device 90 is used for controlling the sequential pulsing of the laser beam 74 from laser device 70, and includes a sequencer laser control module 92 for controlling the laser 70 to sequentially emit a series of pulses of coherent light energy when the laser operator depresses the pulse firing button 118 on laser handpiece 110. The sequencer laser control module 92 may be in the form of a microprocessor or an electronic timing device. The series of pulsed laser beams 74 will destroy and permanently remove the plurality of hair follicles 20 from the skin area 14 of a patient, as shown in FIGS. 1 to 3 of the drawings. The laser sequence control device 90 includes a substantially rectangular shaped housing 94 for holding the sequencer laser control module 92 therein. Housing 94 includes a front wall 98 with openings 100 for receiving electrical line 142 from laser device 70, such that electrical line 142 is connected to the sequencer laser control module 92; and includes a rear wall 104 having an opening 106 for receiving an electrical line 154, such that electrical line 154 connects the electrical panel box 140 to the sequencer laser control module 92, and having an opening 108 for receiving of electrical line 152, such that electrical line 152 connects the pulse firing button 118 to the sequencer laser control module 92.

As shown in FIG. 1, the front wall 46 of housing 40 includes an opening 54 for receiving the fiber optic bundle 76 from laser device 70. The rear wall 48 includes a first opening 56a for receiving power line 146 connected to the electrical panel box 140, a second opening 56b for receiving electrical line 152 from the pulse firing button 118 to the sequencer control module 92 of laser sequence control device 90, and a third opening 56c for receiving electrical line 170 from the activation laser switch/button 168 of the foot pedal switch assembly 160 to the sequencer control module 92 of laser control device 90. Top wall 42 includes control panel 120, as well as an opening 58 for receiving an electrical line 150 from laser device 70. The left side wall 50 is removably connected to laser housing 40 via connecting means 51a to 51d and is used as an access panel 50 for ease of access by the laser operator for repairing and maintaining the laser device 70, the sequence control device 90 and the electrical panel box 140 thereof.

The optical delivery system includes a laser handpiece 110 used for delivering and emitting the series of sequentially pulsed laser beam 74 from laser device 70, via sequencer control module 92 of sequence control device 90. Laser handpiece 110 includes a laser dispersal member 112 having a laser portal opening 114 for receiving fiber optic bundle 76 and a lens 117 for emitting the laser beams 74 of laser device 70. Laser handpiece 110 further includes a hand gripping/holding section 116 having a pulse firing button 118 thereon. Pulse firing button 118 is electrically connected to the sequencer control module 92 of sequence control device 90 via electrical line 152. In addition, laser handpiece 110 is attached at end 95a to fiber optic bundle 76. The fiber optic bundle 74 is sheathed within a flexible conduit 78 for protecting the fiber optic bundle 76.

An alternate optical delivery system is available in the form of an articulated laser arm assembly 210 and may be used in place of the fiber optic bundle 76 connected to laser device 70, and laser handpiece 110. The articulated laser arm assembly 210 is also used for transmitting the series of sequentially pulsed laser beams 74 from laser device 70. Sequence control device 90 operates in the same manner as in the preferred embodiment. The articulated laser arm assembly 210 is located on the corner section 42c of top wall 42 and is adjacent to the laser control panel 120 of laser housing 40, as depicted in FIG. 1A of the drawings. Articulated laser arm assembly 210, as shown in FIG. 1A, includes a first arm member 212 pivotally attached to a second arm member 214. As is know in the art, articulated laser arm assembly 210 further includes a first mirror 216, a second mirror 218 and a third mirror 220 for reflecting the series of sequential coherent light beams (laser beams 74) through the first and second arm members 212 and 214, respectively. Additionally, articulated laser arm assembly 210, also includes a laser handle member 222 pivotally attached to the second arm member 214. Laser handle member 222 includes a gripping/holding section 224 having a pulse firing button 226 is thereon, and a laser dispersal member 228 having a laser portal opening 230 for emitting the series of pulsed laser beams 74 of laser device 70. The articulated laser arm assembly 210 further includes a base member 236 for attaching to the corner section 42c of top wall 42. Pulse firing button 226 is electrically connected to the sequencer control module 92 of sequence control device 90 via electrical line 152.

Another optical delivery system which may be used is a lens system connected to a common optical delivery path connected to the handpiece. In this arrangement, the output of laser 70 is directed to an angled lens which directs the light to the common optical delivery path. Other optical delivery systems, such as a light path or pipe for a diode laser, may be used.

As shown in FIG. 6, laser device 70 is electrically connected to the sequencer laser control module 92 of laser sequence control device 90 via electrical line 142, as well as to the electrical panel box 140 via electrical line 144. Electrical power line 146 and plug 148 for a wall electrical outlet (not shown) are connected to the electrical panel box 140 via power line 146. Laser device 70 is also electrically connected via electrical line 150 to the laser programmable control panel 120. The pulse firing button 118 of laser handpiece 110 is electrically connected to the sequencer laser control module 92 via electrical line 152. The activation laser switch/button 168 of foot pedal switch assembly 160 is electrically connected to the sequencer laser control module 92 via electrical line 170. The sequencer laser control module 92 is electrically connected to the electrical panel box 140 via electrical line 154.

The laser programmable control panel 120 is used for controlling the various output functions of energy/power level, in Joules/centimeters$^2$ (J/cm$^2$), the irradiation pulse width duration in milliseconds (ms)k, the pulse delay in milliseconds (ms) and the laser beam diameter in millimeters (mm) for the single laser device 70. Control panel 120 includes a plurality of control members 122 to 130 and a visual display screen 132 having a keyboard 134 for programming the aforementioned output functions of energy/power level, pulse width duration, pulse delay, and laser beam diameter 75. The control members include an ON/OFF button 122 for activating and de-activating the laser device 70; a control knob/selector 124 for adjusting the energy/power level of the laser device 70; a control knob/selector 126 for adjusting the irradiation pulse width duration (ms) of laser beam 74 of the laser device 70; a control knob/selector 128 for adjusting the pulse delay of the de-activation time (ms) of laser beam 74 of the laser device 70; and a control knob/selector 130 for adjusting the laser beam diameter 75 of the laser device 70. Control panel 120 is electrically connected to laser device 70 via electrical line 150, as shown in FIG. 6.

As an alternate to the pulse firing button 118, a foot pedal switch assembly 160 may be used for initiating the firing sequence of the series of laser beam 74 from laser device 70. Foot pedal switch assembly 160, as shown in FIG. 1 of the drawings, includes a foot pedal base 162 and a foot pedal 164 being connected to the is base 162 by a hinge 166. Foot pedal base 162 includes an activation laser switch/button 168 being electrically connected to the sequencer control module 92 via electrical line 170.

Method of the Present Invention

As depicted in FIG. 3, the plurality of hair shafts 12 project below the epidermis region 16 of skin area 14 and into the dermis region 18. Each hair shaft 12 extends down the follicle 20 and includes a sebaceous gland 22 and which at the anagen stage of the hair cycle further includes a follicular papilla 24 within the hair bulb 26 of hair shaft 12. The follicular papilla 24 is supplied with a plurality of small blood vessels 28 that provide the plurality of growing hair shafts 12 with nourishment. The follicular papilla 24 is an essential structure within the follicle matrix structure 30.

In order to assure destruction of the follicular papilla 24 and permanent hair removal, a sufficient laser energy level is required that does not burn the skin. In addition, the depth of penetration of the series of 74 laser beams must be sufficient to cause permanent removal of hair shaft 12 from the epidermis and dermis regions 16 and 18 of the patient's skin area 14.

Present day single lasers operate at 5 Herz or 5 cycles per second which allows for 200 ms between pulses. The single laser device 70 of laser apparatus 10 of the present invention allows for pulse delays of between 5 ms to 100 ms between pulses with a preferred pulse delay time of 10 ms. The single laser has the capability of sequentially emitting a series of pulses two (2) to six (6) times on the same spot of the patient's skin 14 (e.g. four (4) pulses at 10 Joules/cm$^2$ per pulse each having a pulse width of 10 ms and a delay time between the pulses of 10 ms which allows the delivery of 40 Joules/cm$^2$ to the same spot in 70 ms), as shown by various Examples B through E of FIGS. 5B to 5E, respectively, of the drawings.

As shown in FIGS. 1 through 3 of the drawings, the laser operator (not shown) positions the laser dispersal member 112 of the laser handpiece 110 over a selected treatment area, such as the navel area 34 of the stomach 32 of the patient being treated. The laser dispersal member 112 is positioned, as shown in FIG. 3, by the hand 36 of the laser operator such that the series of pulsed laser beams 74 are substantially perpendicular over the selected treatment area, such as a plurality of hair follicles 20 to be removed. Handpiece dispersal member 112 is positioned at the optimum location for directing the series of laser pulses 74 to strike the plurality of follicular papilla 24 in order to irradiate them in a proper mode. While the handpiece dispersal member 112 is maintained perpendicular to the skin, it is moved parallel to the plane of the skin and along the surface of the skin area 14 for irradiating successive pluralities of hair follicles 20. The handpiece 110 is then moved vertically to the next horizontal line to repeat the removal procedure. The critical regions of the hair follicle matrix structure 30 include hair follicles 20, sebaceous glands 22 and follicular papillas 24 which are irradiated such that the series of pulsed laser beams 74 can be moved across the skin area 14 or otherwise moved over a large are of skin to be treated.

Figure 4:
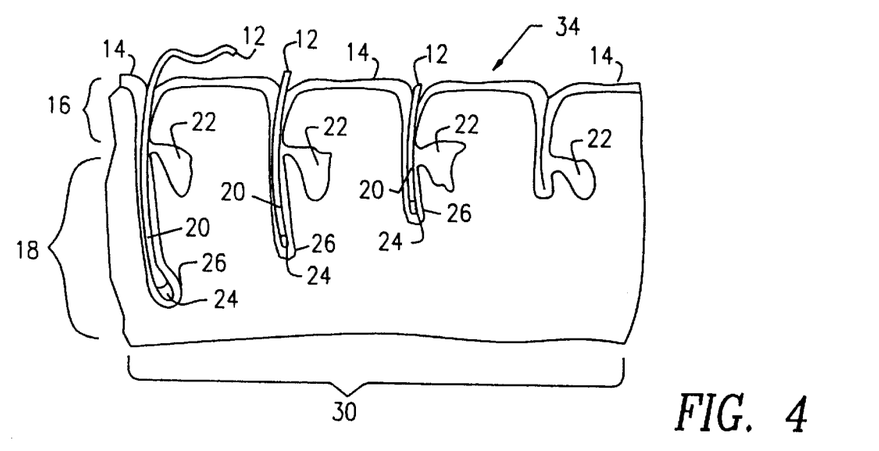
FIG. 4 is a cross-sectional view of a plurality of hair shafts within a region of skin tissue after irradiation by a laser according to the present invention and showing the gradual atrophy of the hair follicle region.

Application of the series of laser pulses 74 to the plurality of hair follicles 20 and to the plurality of follicular papillas 24 causes selective photothermolysis of the hair germinative apparatus, and more particularly, disruption of the hair follicle matrix structure 30 including vaporization of the deposited melanin, capillary destruction of the papillas 24, as well as vacuolation, edema, gas bubbles and protein denaturation. When the laser pulses 74 applied to the plurality of hair follicles 20 are of sufficient level, these effects will seriously injure each of the hair follicles 20 and papillas 24 being irradiated thereby permanently damaging the hair germ 26 which is responsible for hair regrowth which results in permanent hair removal. The initial laser pulse 74 of laser device 70 heats up the hair follicles 20 and subsequent laser pulses 74 supply further heat energy to vaporize the hair follicles 20, as depicted in FIGS. 3 and 4 of the drawings. This sequential pulsing of laser beams 74 two (2) to six (6) times per treatment cycle allows the hair temperature of follicles 20 to increase from room temperature of 38° C. to well over 100° C. for the vaporization of hair follicles 20.

A laser apparatus and method using an improved and programmable single laser has been provided which, by dividing the laser energy delivery into multiple, individually adjustable pulses, with an adjustable delay between the pulses, allows it to achieve permanent hair removal without burning the skin on both light and dark skinned patients having either fine or coarse hair. The pulse repetition rate (the delay between pulses) is less than the thermal relaxation time (TRT) of the hair being treated, and preferably is longer than the thermal relaxation time (TRT) of the patient's skin 14. This single laser apparatus provides for 1) adjusting the pulse width and fluence of the laser; 2) an improved optical delivery system, so that each fired pulse is delivered to precisely the same spot; 3) the operator to precisely define the delay between pulses, and adjust this delay according to clinical variables, such as skin color, hair color, and hair coarseness; and 4) the delivery of these pulses much more rapidly than previous single long pulse lasers of the prior art, so that the delay between pulses is less than the TRT of the patient's skin 14. Treatment may therefore be customized according to skin color, hair color, hair diameter, and the anatomic site being treated, as depicted by Examples G and H of FIGS. 5G and 5H, respectively.

The new technology requires that high energy laser pulses be delivered in rapid succession to exactly the same area of the skin. The maximal energy is delivered to the hair germinative apparatus using two or more long sequential pulses from the single laser, with the pulses repeated at a time interval shorter than the thermal relaxation time of the hair being treated. For most patients, this means two or more high-energy (10–40 Joules/cm$^2$) long duration (2 to 30 milliseconds) pulses, separated by 10 to 30 milliseconds, each with a large (e.g., 10 millimeters or greater) spot size. None of the currently-produced lasers are able to produce these results. The 10 to 30 milliseconds delay between pulses must be selected to be shorter than the thermal relaxation time of the hair being treated, so the hair does not cool off between the pulses.

For example, short pulse duration lasers (with a pulse duration measured in nanoseconds) can repeat rapidly, but these are not suitable for optimal hair removal. All of the new hair removal lasers (ruby, alexandrite, diode) are long pulse lasers. Most of these recycle every 1000 milliseconds, with the fastest recycling every 200 milliseconds. The repetition rate that is necessary, however, is over ten times faster. The new laser apparatus of the present invention is able to accomplish these goals.

The clinical circumstances which the laser operator encounters include situations where the characteristics of the laser energy must be dramatically changed in order to deliver maximal energy without skin damage. The reason for this is that many variables affect the way laser energy is absorbed. For instance, dark hair absorbs more laser energy than light hair, as does dark skin. Coarse hair retains the heat caused by absorption of laser energy longer than fine hair, and skin cools faster than hair. By taking advantage of these differential rates of heating and cooling one can fashion a series of laser energy pulses that will selectively remove hair.

For example, an African-American patient with brown skin and coarse, black hair would need to have the energy delivered slowly with a relatively long delay between pulses. However, the optimal time delay selected is not long enough to allow the hair to cool, but is long enough to allow the skin to cool. In this manner, the delay between pulses is selected to be less than the TRT of the hair, but more than the TRT of the skin. The second pulse is then emitted, heating the hair more, this time causing permanent destruction of the hair. The skin again heats up, but not enough to cause damage. As shown by Example E of FIG. 5E, the first laser pulse 74 is long, e.g. 20 ms, with low energy (e.g. 10 Joules/cm$^2$). The time delay would be relatively long (e.g. 40 ms), and then the second laser pulse 74 (from the same laser device 70) is emitted with a long pulse width (e.g. 15 ms) and low energy (e.g. 8 Joules/cm$^2$). Thus, 18 Joules/cm$^2$ is delivered safely to a patient in whom 12 Joules/cm$^2$ delivered in a single pulse might burn the skin. (Present day single lasers cannot emit a long pulse of this energy level this rapidly).

A Caucasian patient with light brown, fine hair, and light, untanned skin requires much greater energy delivered in order to achieve permanent hair removal. Light, fine hair absorbs little laser energy, but even light skin will absorb some laser energy, which is why pulsed energy delivery, with a delay to allow skin cooling, allows the delivery of more laser energy, safely, to the hair germinative apparatus. In this situation, as shown by Example F of FIG. 5F, one would use a relatively short first laser pulse 74 (e.g. 5 ms) with a high energy level (e.g. 35 Joules/cm$^2$) from laser device 70; a short time delay between pulses (e.g. 10 ms) since light skin cools faster; and a short second laser pulse 74 (e.g. 5 ms) with a somewhat less energy level (e.g. 20 Joules/cm$^2$) from the single laser device 70. Thus, 55 Joules/cm$^2$ are thereby delivered safely in two pulses to a patient in whom 40 Joules/cm$^2$ delivered in a single pulse might burn the skin.

Figure 5A:
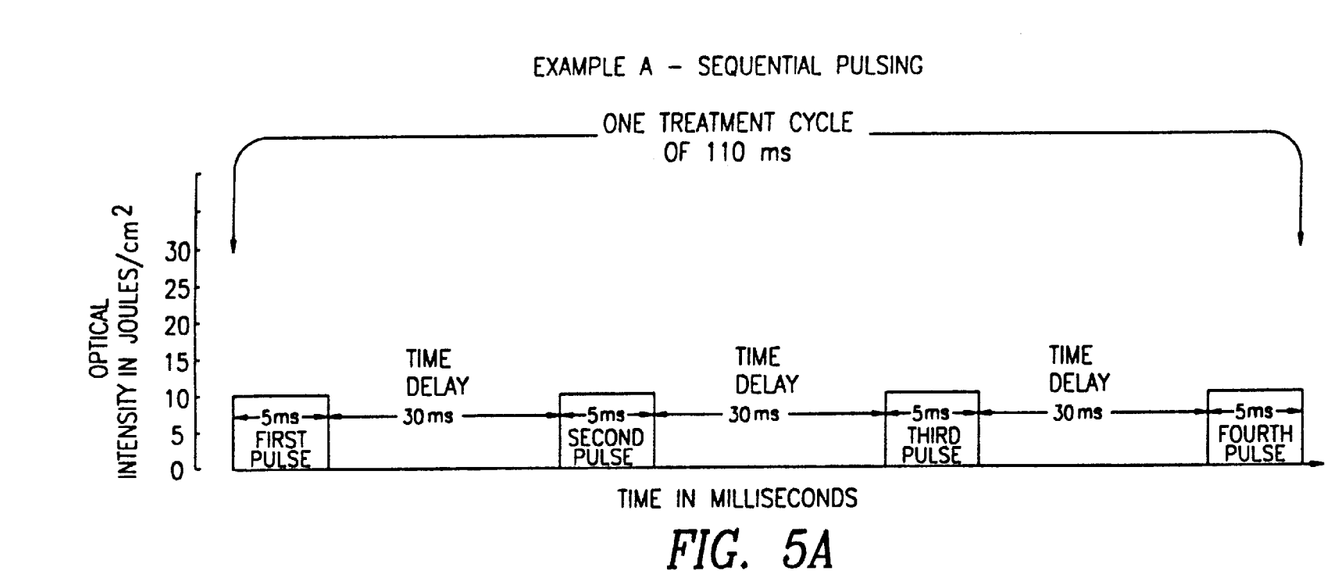
FIG. 5A is a graph showing the time profile and the optical intensity field performance for the lasers used during the hair removal process.
Figure 5B:
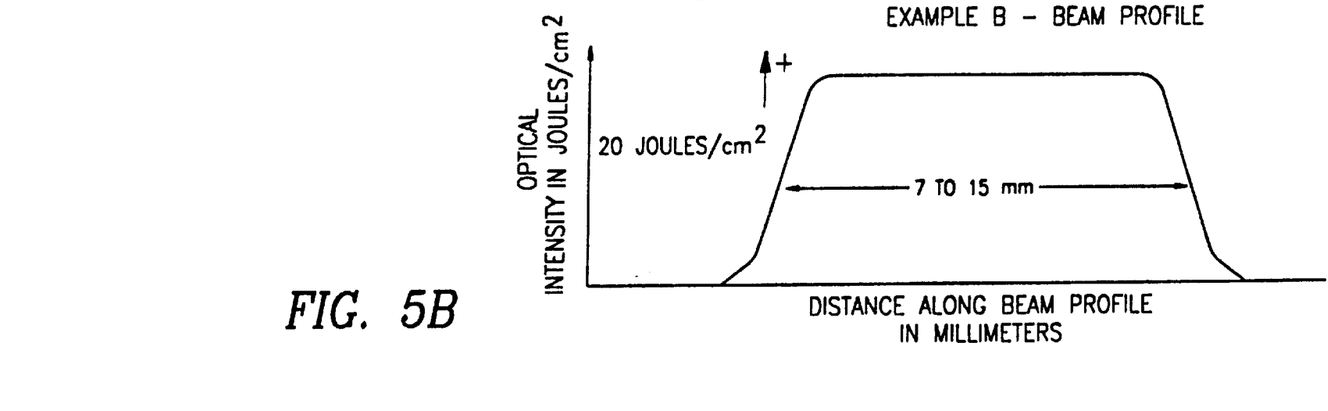
FIG. 5B is a graph showing the distance profile and the optical intensity field performance for the lasers used during the hair removal process.
Figure 5C:
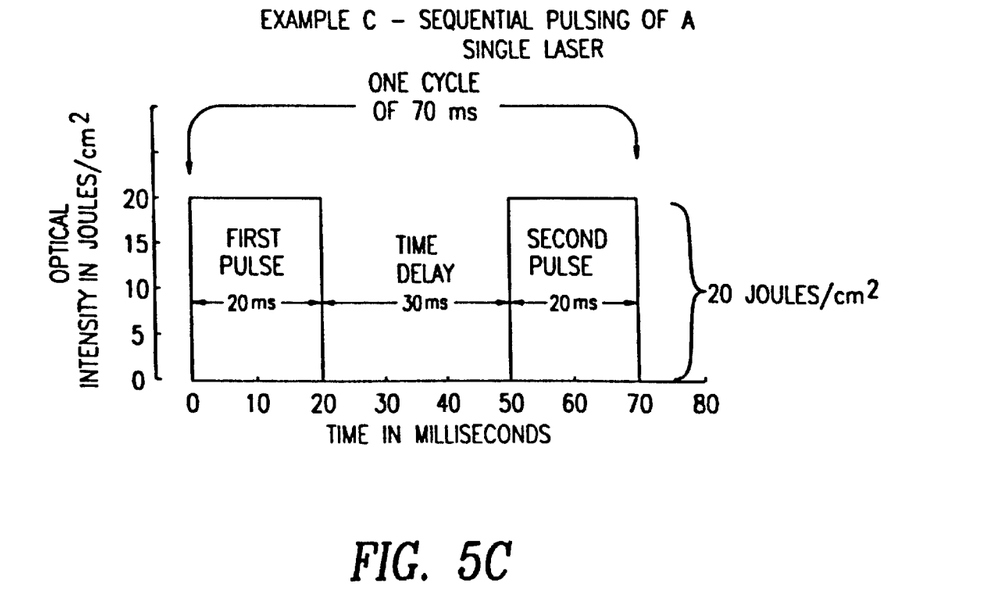
FIG. 5C is a graph showing the time profile and the optical intensity field performance for the sequential pulsing of coherent light energy of a single diode laser for the hair removal process.

The actual irradiating of the plurality of hair follicles 20 is accomplished by the laser operator depressing the pulse firing button 118 of laser handpiece 110 which in turn emits a series of laser pulses 74 in a sequenced pulsed cycle over the designated treatment area 30, as shown in FIGS. 2, 3, 5A of the drawings. In one example, a series of laser pulses 74 of single laser device 70 are sequentially pulsed for an irradiation time of preferably 5 to 10 milliseconds (ms) per pulse (irradiation time can be varied in the range of ½ to 40 milliseconds for each of the laser pulses 74), with a pulse delay duration time between pulses of preferably 15 to 20 milliseconds for cooling the skin area 14 in order to prevent burning (pulse delay duration time can be varied in the range of 5 to 100 milliseconds (ms) for each of the laser pulses 74 of laser device 70 being pulsed onto the skin of the patient). A series of sequential irradiation pulses may be emitted two (2) to six (6) times for a complete treatment cycle, as shown in FIG. 5A, which is sufficient to permanently remove the plurality of hair follicles 20 of the patient's skin area 14 being treated.

Figure 5D:
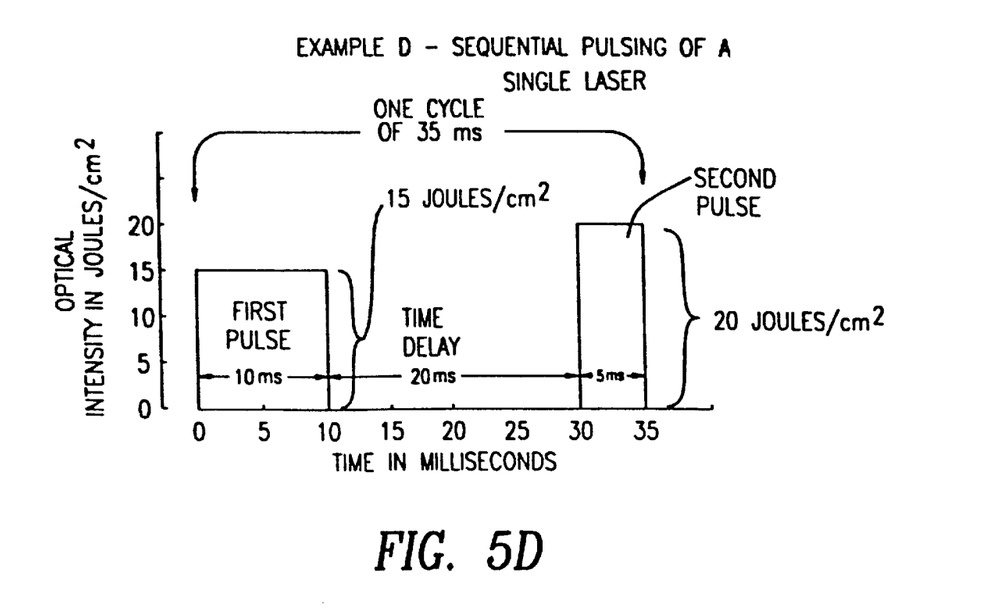
FIG. 5D is a graph showing the time profile and the optical intensity field performance for the sequential pulsing of coherent light energy of a single alexandrite laser for the hair removal process.
Figure 5E:
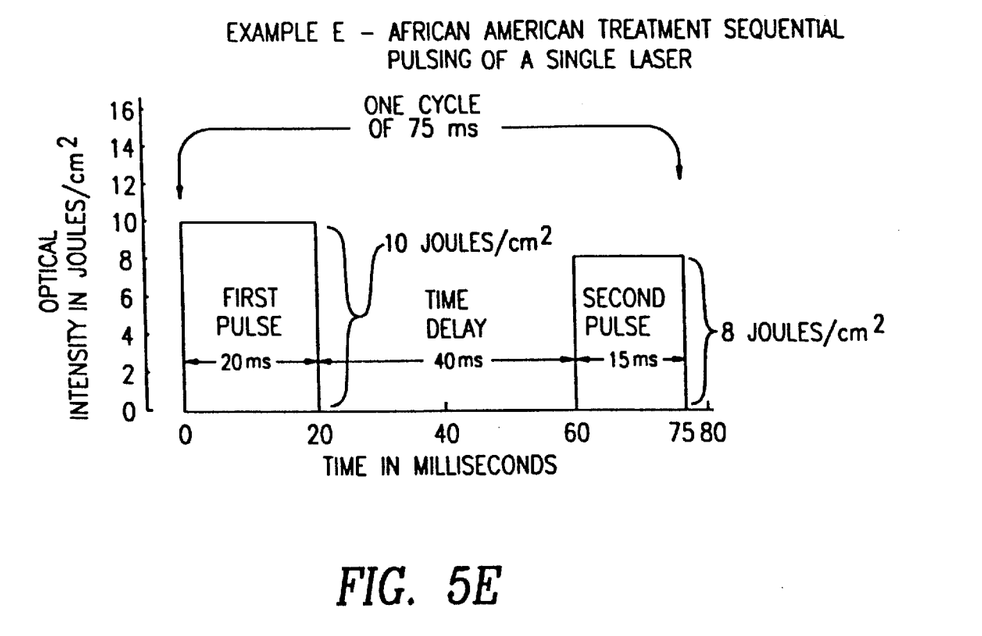
FIG. 5E is a graph showing the time profile and the optical intensity field performance for the sequential pulsing of coherent light energy of a single laser for the hair removal process and treatment of African-American patients.
Figure 5F:
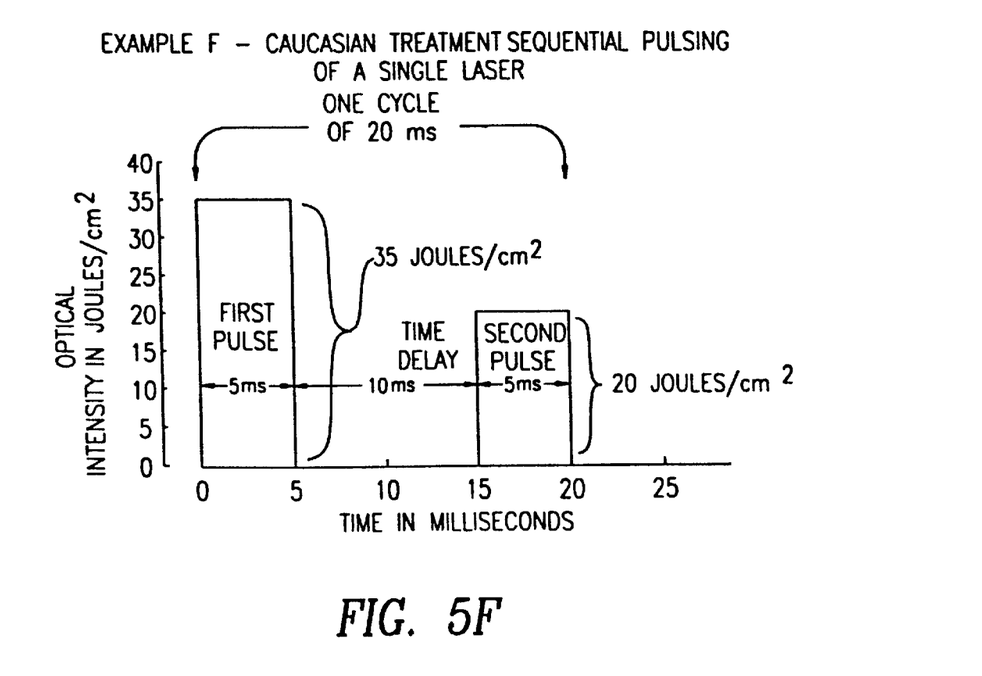
FIG. 5F is a graph showing the time profile and the optical intensity field performance for the sequential pulsing of coherent light energy using a single ruby laser for the hair removal process and treatment of Caucasian patients.
Figure 5G:
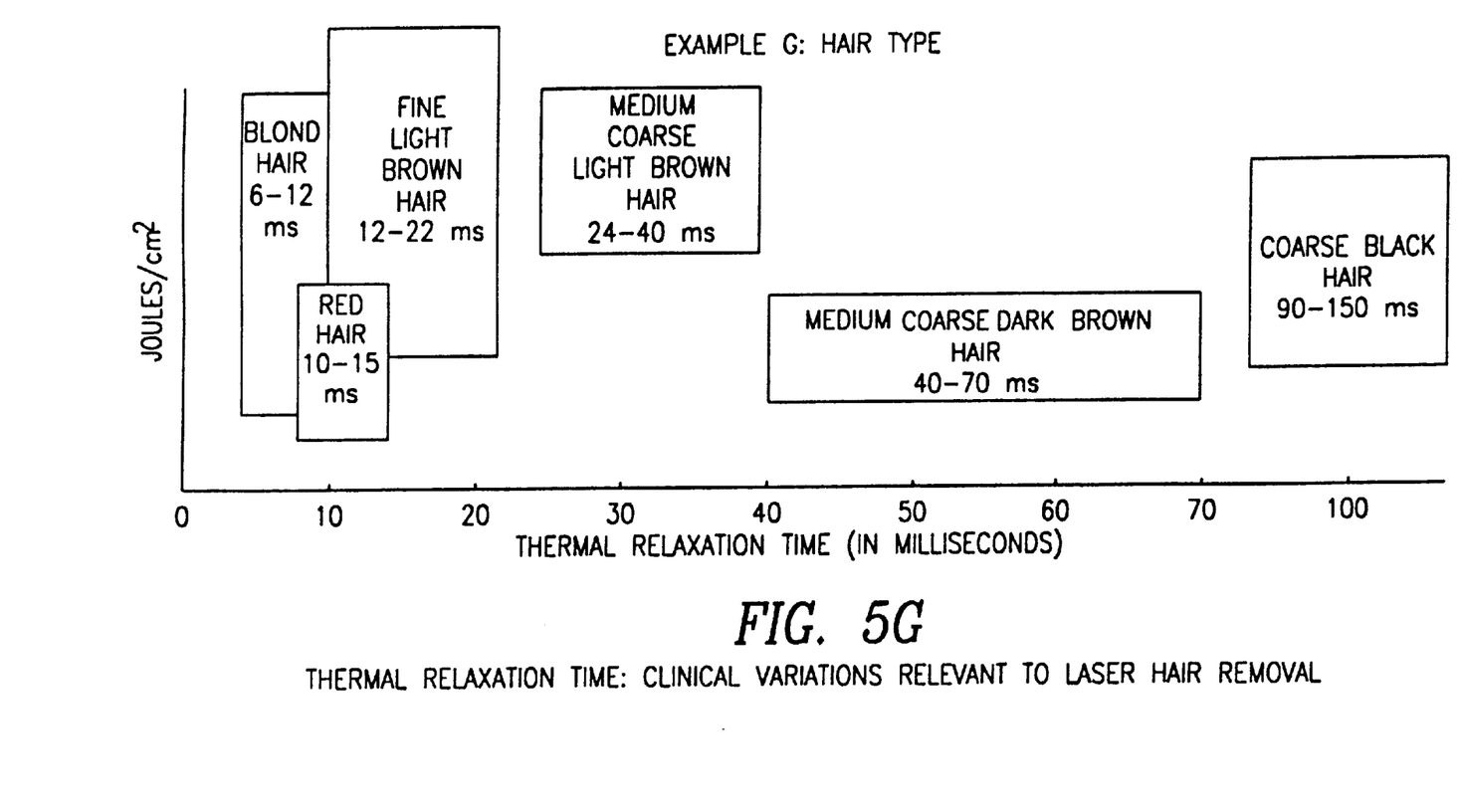
FIG. 5G is a graph showing the thermal relaxation time (TRT) profile and the optical intensity field performance of different hair types for the hair removal process.
Figure 5H:
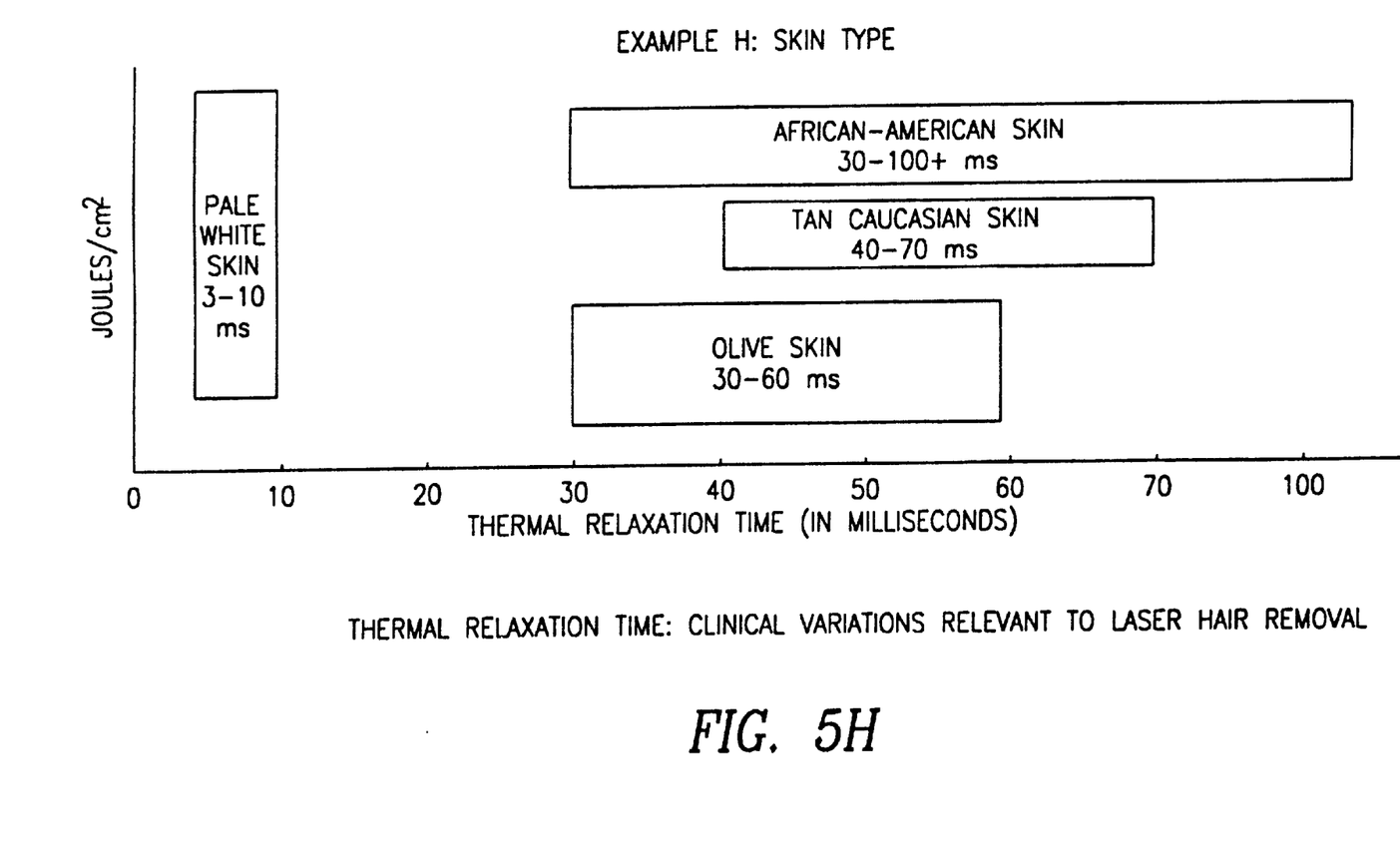
FIG. 5H is a graph showing the thermal relaxation time (TRT) profile and the optical intensity field performance of different skin types for the hair removal process.

In the specific Example D of a two (2) pulse cycle, as shown in detail by FIG. 5D, laser 70 is controlled by sequence control device 90 so that laser 70 emits a 10 ms pulse at an energy level of 15 Joules/cm$^2$, then there is a 20 ms delay, and then laser 70 emits another sequential 5 ms pulse at an energy level of 20 Joules/cm$^2$ to the same spot. This short delay between pulses is enough time to allow the spot being treated to dissipate heat and slightly cool the skin 14 so that it can receive more energy (e.g. 35 Joules/cm$^2$) safely without burning the skin and permanently remove the hair. In addition, the 35 Joules/cm$^2$ is enough energy to burn the hair follicles over a larger spot size (e.g. 15 mm v. 10 mm) so that a larger area of the patient can be treated in substantially less time. Spot size 75 may be circular or rectangular and a grid pattern may be used for ease of moving handpiece assembly 110 across the patient's skin 14.

The foregoing procedure is possible with the present invention because this single laser is operating with a sequencer control device 90 and this allows the time between pulses to be controlled and substantially reduced, e.g. 20 ms. This short delay between the pulses is enough time to allow the spot being treated to dissipate heat and cool so that it can receive more energy (e.g. 35 Joules/cm$^2$) safely without burning the skin and permanently remove the hair. In addition, the 35 Joules/cm$^2$ is enough energy to burn the hair follicles over a larger spot size (e.g. 15 mm v. 10 mm) so that a larger area of the patient can be treated in substantially less time. Laser 70 may be pulsed in a number of different modes to obtain the desired result, which includes the sequential pulsing, as described above.

Another treatment cycle, as shown in Example A of FIG. 5A, for permanently removing hair follicles 20 using a single laser 70 would have the laser operator pulsing the laser beam 74 at an energy level of 10 Joules/cm$^2$ per pulse with an irradiation pulse duration of 5 ms per pulse for a series of four (4) pulses. The time delay between each of the 4 pulses would be 30 ms so there would be three (3) time delays between the four (4) irradiation pulses. The complete treatment cycle includes pulsed irradiation time (4×5 ms) of 20 ms plus three (3) time delay segments (3×30 ms) of 90 ms for a total treatment cycle time (20 ms+90 ms) of 110 ms at a total energy level of 40 Joules/$^2$ (4 pulses×10 Joules/cm$^2$ per pulse). This treatment cycle is sufficient to safely and permanently remove the plurality of hair follicles 20 being treated by laser pulses 74 of the single laser apparatus 10, as shown in FIGS. 3 and 5A of the drawings.

In another example, the laser operator may want laser device 70 to operate and emit a series of pulses of laser beams 74 sequentially at different pulse durations of 5 ms, 4 ms, and 3 ms with a delay time of 20 ms and 15 ms between the pulses, at an energy level of 15 Joules/cm$^2$ per pulse, with a laser beam diameter 75 of 10 millimeters. For this specific treatment cycle the operator would program the above data into the programmable control panel 120, as shown in FIG. 5A of the drawings, in the following manner. The laser operator initiates the programming of this specific treatment cycle by turning ON the control panel 120 via ON/OFF button 122. The operator then selects and activates the control knob 124 for adjusting the power level to 15 Joules/cm$^2$ for laser device 70, and then the operator keys in the 15 Joules/cm$^2$ via keyboard 134 for each of the 5 ms, 4 ms and 3 ms pulses and this data is then visually displayed on display screen 132. If the power level for each pulse duration is correct the operator presses the "ENTER" key on keyboard 134 in order to enter the data in control panel 120. Next, the laser operator then selects and activates the control knob 130 for adjusting the laser beam diameter 75 of laser device 70 to be a 10 millimeter diameter. Then the operator keys in the 10 millimeters for laser beam diameter 75 via keyboard 134 for each of the 5 ms, 4 ms and 3 ms pulses, and this data is then visually displayed on display screen 132. If the laser beam diameter 75 for each pulse duration is correct the operator presses the "ENTER" key on keyboard 134 in order to enter this data in control panel 120. The next step of programming by the laser operator is the selection and activation of the control knob 126 for pulse duration of laser 70, at which time the operator then keys in the aforementioned data/information via keyboard 134 so that the first pulse duration is 5 ms, the second pulse duration is 4 ms and the third pulse duration is 3 ms, and it is then visually displayed on display screen 132. If the series of pulse durations are correct the operator presses the "ENTER" key on keyboard 134 to enter the above data into the programmable control panel 120. The last step of programming by the laser operator is the selection and activation of the control knob 128 for pulse delay time between irradiation pulses of laser device 70, at which time the operator then keys in the aforementioned information via keyboard 134 so that the first pulse delay time of 20 ms is between the pulses of 5 ms and 4 ms, and the second delay time of 15 ms is between the pulses of 4 ms and 3 ms, and it is then visually displayed on display screen 132. If the series of time delays between pulses are correct, the operator presses the "ENTER" key on keyboard 134 to enter the above information/data in the programmable control panel 120.

Laser apparatus 10 is now ready to fire the series of laser pulses 74 as programmed. Laser operator depresses the pulse firing button 118 over the selected treatment area 34 to start the pulsed treatment cycle. There is a first pulse irradiation time of 5 ms followed by a first time delay of 20 ms, sequentially followed by a second pulse irradiation time of 4 ms followed by a second time delay of 15 ms, and sequentially followed by a third pulse irradiation time of 3 ms. The complete treatment cycle of pulsed irradiation and delay times is thus 47 milliseconds at a total energy level of 45 Joules/cm$^2$ (three (3) pulses at 15 Joules/cm$^2$ per pulse) which is sufficient to permanently remove the plurality of hair follicles 20 of the patient's skin area 14 being treated by laser beams 74 of laser apparatus 10, as shown in FIG. 3 of the drawings.

Alternatively, the articulated laser arm assembly 222 with laser dispersal member 228 and pulse firing button 226, as shown in FIG. 1A, is operated in a similar manner as in the preferred embodiment described above. Other optical delivery systems, such as a light path or pipe for a diode laser, may be used to deliver laser energy to the skin without requiring use of a fiber optic delivery system.

As shown in FIG. 4, the laser-damaged follicles 20 will gradually recede due to destruction of the follicle matrix structure 30, including disruption of blood flow from the blood vessel capillaries 28 to each of the papillas 24. The hair follicles 20 show gradual atrophy without a blood supply thereby causing permanent hair removal.

Different types of hair and skin pigmentation, and different cooling times of the epidermis, and hair follicles of different sizes, as well as the location of body hair to be removed will require different methods of laser treatment to fit the individual needs of the patient undergoing the therapeutic laser treatment for permanent hair removal. This laser treatment of sequentially pulsed laser beams 74 allows the laser operator to individually adjust each of the output functions of energy/power level, pulse width duration, pulse delay and laser beam diameter 75 for the particular patient by using control panel 120 which controls the single laser device 70 of laser apparatus 10 of the present invention.

Advantages of the Present Invention

Accordingly, an advantage of the present invention is that it provides an improved laser apparatus and method which supplies a series of high level laser energy pulses to heat a hair follicle and hair follicle shaft to cause permanent damage to that hair follicle and shaft, and yet spare the skin from burning, thus providing a safe and permanent method of hair removal.

Another advantage of the present invention is that it provides for an improved laser apparatus employing a single laser, controlled by a sequence control device, and a fiber optic cable which sequentially emits a series of pulses of coherent light energy from the fiber optic cable for permanently removing a plurality of hair follicles, veins or capillaries from the skin area of a patient.

Another advantage of the present invention is that it provides for an improved laser apparatus having a handpiece for ease of use by the operator in directing the series of laser pulses at the skin to rapidly remove large areas of hair on almost any body area, such as on the face, hands, arms, legs, breasts, stomach and the like, where such treatment provides a low discomfort level to the patient.

Another advantage of the present invention is that it provides for an improved laser apparatus and method for treatment of other cutaneous conditions (in addition to hair), such as the treatment of leg veins, spider veins, angiomas, lesions, other vascular anomalies and other dermatological conditions effecting the skin of a patient.

Another advantage of the present invention is that it provides a single pulsed laser and a sequence control device for emitting laser energy through a common optical delivery system which delivers sequential pulses from the single pulsed laser.

Another advantage of the present invention is that it provides for an improved laser apparatus and method for adjusting pulse width and the time delay between pulses to customize treatment and the energy delivered to the spot being treated according to skin color, hair color, hair diameter and the anatomic site being treated.

Another advantage of the present invention is that it provides safe and permanent hair removal in a wider range of patients having hairs of all colors and skin of all colors, including patients with dark skin. Generally, the present invention will accommodate all persons having hair which is darker than their skin.

Another advantage of the present invention is that it provides a delay between laser pulses which is shorter than the thermal relaxation time of the hair being treated, so the hair does not cool off between pulses, and wherein the delay between laser pulses is longer than the thermal relaxation time of the skin, so the skin may dissipate heat and cool off between pulses and does not burn.

Another advantage of the present invention is that it provides a method and apparatus wherein the pulse width and delay between pulses may be varied to accommodate the thermal relaxation time of each patient's hair and skin.

Another advantage of the present invention is that it provides for an improved laser apparatus and method that is easy to use, and the laser apparatus is durable, light-weight and easily maintained.

Another advantage of the present invention is that it provides for an improved laser apparatus that provides a wider beam area (spot size on the skin) by utilizing a single pulsed laser and a sequence control device for delivering more laser energy to each spot allowing the spot size to be made larger for faster treatment.

A further advantage of the present invention is that it provides for an improved laser apparatus that is simple to manufacture and assemble in an economical manner, and is cost effective for the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A laser apparatus for permanently removing a plurality of hair follicles from the skin of a patient, comprising:
    a) a housing having a single laser for sequentially emitting a series of pulses of coherent light energy each having a pulse width in the range of ½ ms to 40 ms; being a parametrically defined pulse group;
    b) an optical delivery means connected to said laser for transmitting said series of pulses of coherent light energy to the same spot on the skin of a patient for removing hair follicles;
    c) means for controlling said laser to emit said series of pulses of coherent light energy sequentially, with a time delay of less than 100 milliseconds between each of said pulses; and
    d) a handpiece for holding a section of said optical delivery means for directing said series of pulses of coherent light energy to the same spot of the patient's skin to remove the plurality of hair follicles.

2. A laser apparatus in accordance with claim 1, wherein said means for controlling includes a sequencer device having a control module for controlling and modulating the sequential pulsing of said laser to sequentially emit said series of pulses of coherent light energy, and for controlling the time delay between said sequential pulses to less than 100 milliseconds between each of said pulses.

3. A laser apparatus in accordance with claim 2, wherein said control module is in the form of a microprocessor or an electronic timing device.

4. A laser apparatus in accordance with claim 2, further including an electrical panel box for supplying electrical power to said laser and to said sequencer device.

5. A laser apparatus in accordance with claim 1, wherein said optical delivery means is connected to said handpiece, said handpiece having a laser portal opening and lens for directing said series of pulses of coherent light energy on the same spot on the patient's skin.

6. A laser apparatus in accordance with claim 1, wherein said optical delivery means includes a multi-strand fiber optic bundle for transmitting said series of pulses of coherent light energy.

7. A laser apparatus in accordance with claim 6, further including a foot pedal switch assembly for pulsing said laser to emit said series of pulses of coherent light energy sequentially through said fiber optic bundle for removing the plurality of hair follicles from the same spot on the skin of a patient.

8. A laser apparatus in accordance with claim 1, wherein said optical delivery means includes a light path or pipe for transmitting said series of pulses of coherent light energy.

9. A laser apparatus in accordance with claim 1 wherein said handpiece includes a pulse firing button for sequentially pulsing said laser to sequentially emit said series of pulses of coherent light energy for removing the plurality of hair follicles from the same spot on the skin of a patient.

10. A laser apparatus in accordance with claim 1, wherein said laser is an alexandrite laser or a diode laser.

11. A laser apparatus in accordance with claim 1, wherein said laser is a ruby laser or an infrared laser.

12. A laser apparatus for permanently removing a plurality of hair follicles from the skin of a patient, comprising:
    a) a housing having a single laser for sequentially emitting a series of pulses of coherent light energy each having a pulse width in the range of ½ ms to 40 ms; being a parametrically defined pulse group;
    b) light transmission means connected to said laser for transmitting said series of pulses of coherent light energy to the same spot on the skin of a patient for removing hair follicles;
    c) means for controlling said laser to emit said series of pulses of coherent light energy sequentially, with a time delay of less than 100 milliseconds between each of said pulses; and
    d) a handpiece for holding a section of said light transmission means for directing said series of pulses of coherent light energy to a selected spot of the patient's skin to remove the plurality of hair follicles.

13. A laser apparatus in accordance with claim 12, wherein said light transmission means includes a multi-strand fiber optic bundle for transmitting said series of pulses of coherent light energy.

14. A laser apparatus in accordance with claim 12, wherein said light transmission means includes articulated arms having at least two movable sections with mirrors for transmitting the series of pulses of coherent light energy.

15. A laser apparatus in accordance with claim 14, wherein said articulated arms are connected to said handpiece, said handpiece having a laser portal opening for directing said series of pulses of coherent light energy on the same spot on the patient's skin.

16. A laser apparatus in accordance with claim 12, wherein said means for controlling includes a sequencer device having a control module for controlling and modulating the sequential pulsing of laser to sequentially emit a series of pulses of coherent light energy, and for controlling the time delay between said sequential pulses to less than 100 milliseconds between each of said pulses.

17. A laser apparatus in accordance with claim 16, wherein said control module is in the form of a microprocessor or an electronic timing device.

18. A laser apparatus in accordance with claim 16, further including an electrical panel box for supplying electrical power to said laser and to said sequencer device.

19. A laser apparatus in accordance with claim 12, wherein said handpiece includes a pulse firing button for sequentially pulsing said laser to sequentially emit said series of pulse of coherent light energy for removing the plurality of hair follicles from the same spot on the skin of a patient.

20. A laser apparatus in accordance with claim 12, wherein said laser is an alexandrite laser.

21. A laser apparatus in accordance with claim 12, wherein said laser is a diode laser.

22. A laser apparatus in accordance with claim 12, wherein said laser is a ruby laser or an infrared laser.

23. A laser apparatus in accordance with claim 12, further including a foot pedal switch assembly for pulsing said laser to emit said series of pulses of coherent light energy sequentially through said light transmission means for removing the plurality of hair follicles from the same spot on the skin of a patient.

24. A method of removing hair from the skin of a patient using a laser apparatus having a single laser, a sequence control device and an optical delivery system, comprising the steps of:

a) controlling said single laser to sequentially emit a series of pulses of coherent light energy, each having a pulse width in the range of ½ ms to 40 ms;

b) transmitting said series of pulses of coherent light energy rough said optical delivery system to the same spot on the skin of the patient;

c) irradiating the same spot on the skin containing the hair with said series of sequential pulses of coherent light energy transmitted through said optical delivery system from said single laser; and d) pulsing said single laser at least two or more times through said optical delivery system at a wavelength in the range of 550 to 1200 nm, at a power level in the range of 5 to 80 Joules/cm$^2$, at a pulse duration in the range of ½ to 40 milliseconds, having a pulse delay in the range of 5 to 100 milliseconds, and having a beam diameter on the treatment area in the range of 4 to 50 millimeters.

25. A method of removing hair from the skin of a patient using a laser apparatus having a single laser, a sequence control device and an optical delivery system, comprising the steps of:

a) controlling said single laser to sequentially emit a series of pulses of coherent light energy, each having a pulse width in the range of ½ to 40 ms;

b) transmitting said series of pulses of coherent light energy through said optical delivery system to the same spot on the skin of the patient;

c) irradiating the same spot on the skin containing the hair with said series of sequential pulses of coherent light energy transmitted through said optical delivery system from said single laser; and d) pulsing said single laser to have a pulse delay between said series of pulses less than the thermal relaxation time (TRT) of the patient's hair and more than the thermal relaxation time (TRT) of the patient's skin in order to remove the patient's hair and in order to avoid burning of the patient's skin, said pulse delay between said series of pulses being less than 100 ms.

* * * * *